United States Patent [19]

Devant et al.

[11] Patent Number: 5,083,021
[45] Date of Patent: Jan. 21, 1992

[54] MASS SPECTROMETER WITH QUADRUPOLE FILTER AND MOVABLE CARRIER PROVIDING ACCESS TO THE ION SOURCE

[75] Inventors: Gérard Devant, Paris; Olivier Maulat, Sannois, both of France

[73] Assignee: Societe Nouvelle Nermag, Suresnes, France

[21] Appl. No.: 644,958

[22] Filed: Jan. 22, 1991

[30] Foreign Application Priority Data

Jan. 26, 1990 [FR] France ................................. 90 00950

[51] Int. Cl.⁵ ........................ H01J 49/00; G01N 27/62
[52] U.S. Cl. ................................... 250/292; 250/289
[58] Field of Search ................. 250/292, 289, 288, 281

[56] References Cited

U.S. PATENT DOCUMENTS 4,595,835 6/1986 Boulin et al. ................... 250/423 R

FOREIGN PATENT DOCUMENTS 1614536 6/1967 Fed. Rep. of Germany .
1289678 3/1961 France .
1370763 7/1964 France ................................ 250/289

OTHER PUBLICATIONS

"Design and Construction of LS/MS Interfaces..." by P. J. Arpino, Int. J. of Mass Spectr. and Ion Processes, 64 (1985) Apr., No. 3, Amsterdam, Netherlands.
"The Review of Scientific Instruments", vol. 43, No. 10, Oct. 1972, pp. 1527-1530, An Electrodynamic Ion Source for the Mass Spectrometry of Liquids, by C. A. Evans, Jr. et al.

Primary Examiner—Jack I. Berman
Assistant Examiner—James E. Beyer
Attorney, Agent, or Firm—Nikolay Parada

[57] ABSTRACT

A mass spectrometer with quadrupole filter comprises a spectrometer chamber containing the ion source, its associated electron optical system, and a quadrupole filter. The chamber is designed in the form of a hollow sleeve closed at one end by a removable leak-tight cover mounted on a longitudinally-sliding motor-driven carriage which also supports the ion source and its optical system. The carriage is capable of selective displacement in translational motion between a closed position in which the ion source is in the work position and the cover is in the closed position, and an open position in which the carriage projects outside the casing at least to a partial extent and allows access to the ion source and its associated optical system.

18 Claims, 2 Drawing Sheets

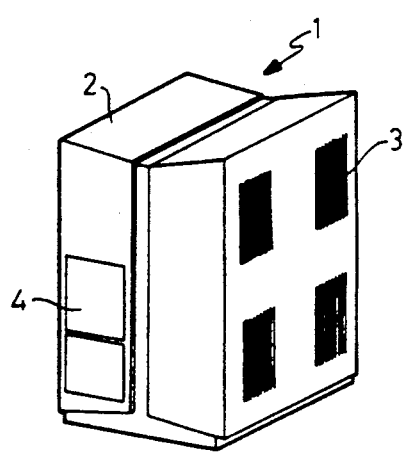
FIG_1
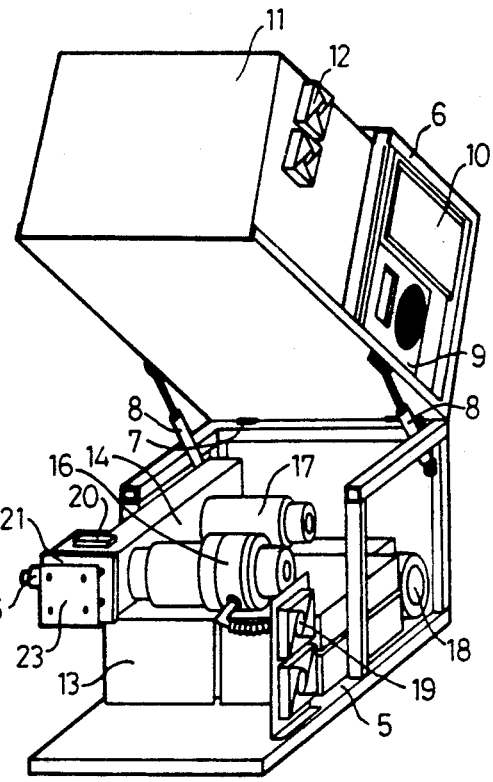
FIG_3
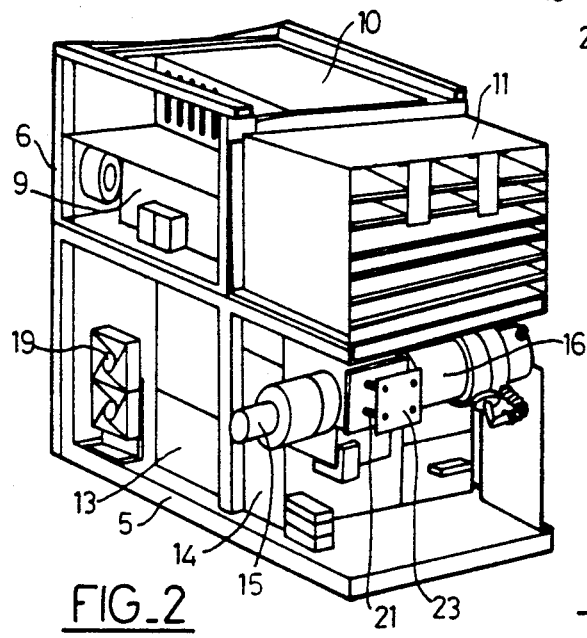
FIG_2
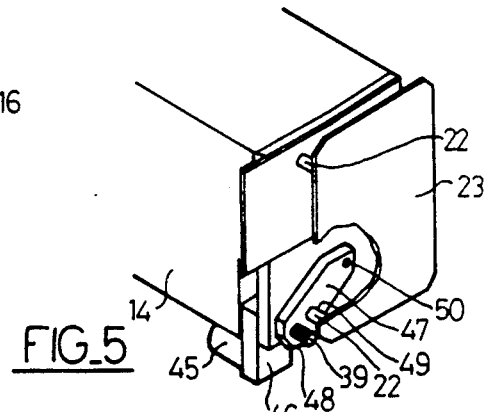
FIG_5
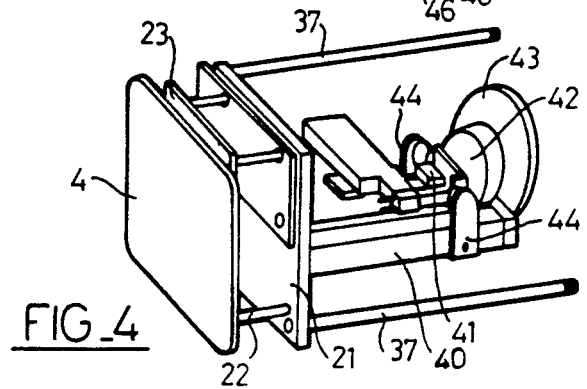
FIG_4

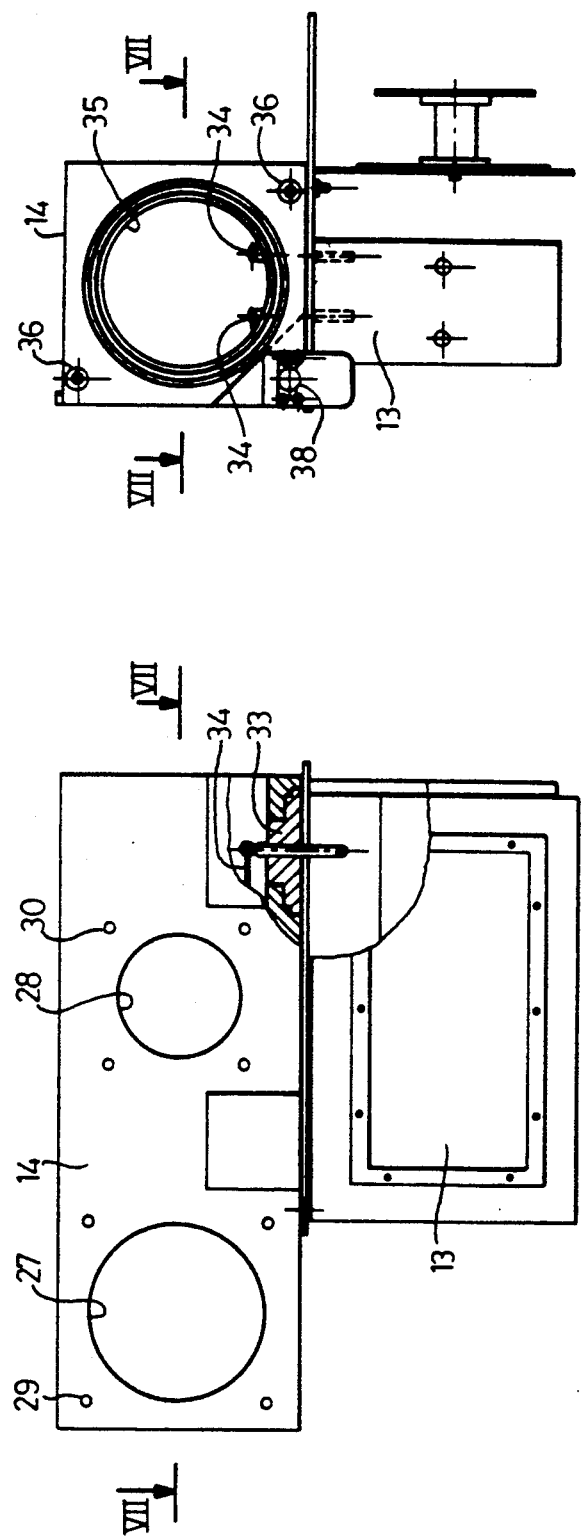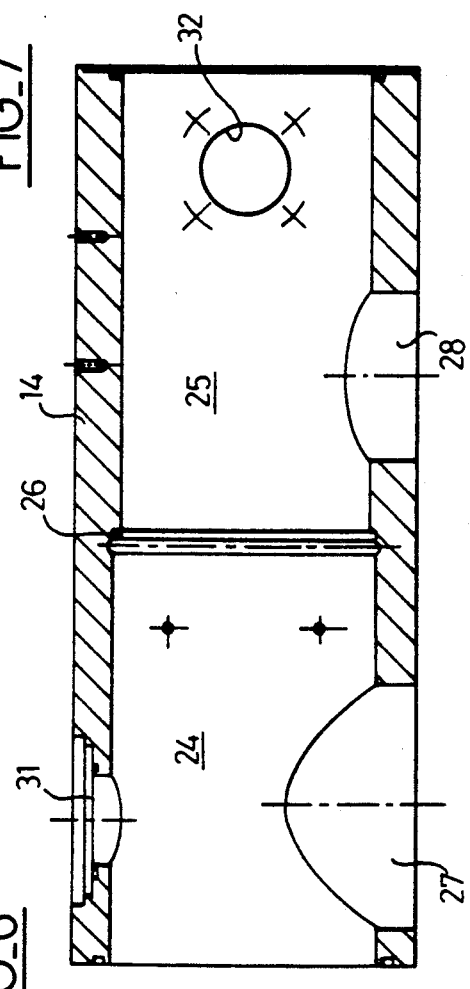

MASS SPECTROMETER WITH QUADRUPOLE FILTER AND MOVABLE CARRIER PROVIDING ACCESS TO THE ION SOURCE

BACKGROUND OF THE INVENTION

1. Field of the Invention

The invention relates to a mass spectrometer with quadrupole filter comprising, within a frame closed by a casing, a spectrometer chamber which is intended to contain the ion source and its associated electron optical system, and a quadrupole filter.

2. Description of the Prior Art

It is known that, in a spectrometer of this type, periodical access to the ion source is necessary for maintenance or modification of the spectrometer characteristics. In devices of the prior art, however, this problem has not been satisfactorily solved since various disassembly operations are required in order to gain access. The object of the invention is to propose an apparatus which provides particularly easy access to the ion source.

SUMMARY OF THE INVENTION

The invention achieves its object by virtue of the fact that the spectrometer chamber is designed in the form of a hollow sleeve closed at one end by a removable leak-tight cover mounted on a motor-driven longitudinally-sliding carriage which also supports the ion source and its optical system, the carriage being capable of selective displacement in translational motion between a closed position in which the ion source is in the work position and said cover is in the closed position, and an open position in which the carriage project outside the casing at least to a partial extent and allows access to the ion source and its associated optical system.

It is readily apparent that the opening or closing movement of the carriage is controlled automatically by means of an order formulated on the data-processing system associated with the spectrometer. The program automatically controls stopping or re-starting of the vacuum pumps, depending on whether leak-tightness of the spectrometer chamber is to be interrupted or restored by opening or closing of the cover.

As an advantageous feature, the carriage is adapted to carry a second closure plate which provides a separation, when the carriage is in the closed position, between two compartments maintained at different pressures. The higher-pressure compartment houses the ion source which is usually associated with a gas-phase chromatographic device (in the so-called GC/MS devices) whilst the lower-pressure compartment houses the analyzer. The second closure plate advantageously cooperates by means of a ring rigidly fixed to the quadrupole filter with an annular shoulder formed in the body of the spectrometer chamber. However, strict leak-tightness is not necessary at this level since the leakage flow can be recovered by the turbomolecular pumps associated with each compartment.

Advantageously, the carriage is mounted on at least one rod guided in translational motion by ball-type slides whilst the carriage is driven by a motor and a reduction-gear unit which are attached to the spectrometer chamber and drive a sliding threaded rod which is attached to the carriage.

For reasons of convenience of positioning, the threaded rod is displaced off-center with respect to the cover but is associated with a bearing arm which is preferably removable and is intended to center the closing force and therefore to ensure uniform leak-tightness of the cover in the closed position.

In accordance with an advantageous feature, the spectrometer chamber has a body which is externally parallelepipedal and internally cylindrical, said body being provided in at least two of its corners with bores which are intended to receive a carriage-guiding rod or a carriage-driving rod.

The body of the spectrometer chamber is made of machined solid metal or metal alloy, for example of aluminum.

In accordance with a characteristic feature of the invention, the quadrupole filter is entirely housed within the spectrometer chamber and is maintained therein by means of spacer rings, thus avoiding any overhang which generates vibrations or resonances.

Advantageously, the quadrupole filter can be introduced into or withdrawn from the spectrometer chamber through the end which is provided with the removable cover, and the filter is connected to the high-frequency transformer by plugging onto short rigid pins.

By means of all these measures (solid chamber body, short connections, quadrupole filter without overhang), the sensitivity of the apparatus to vibrations can be practically eliminated and the mechanical forepump (associated with the turbomolecular pumps) can therefore be directly incorporated with the spectrometer frame instead of being placed separately as in known devices.

With a view to ensuring compatibility between compactness of the assembly and accessibility of the essential parts, the main frame is divided into two superposed sub-frames preferably mounted in articulated relation by means of hinges, and supporting jacks.

The lower sub-frame essentially houses the mechanical elements (in particular the spectrometer chamber, the high-frequency transformer tank, the turbomolecular pumps and the mechanical forepump). The upper sub-frame houses the electrical or electronic elements which are of lighter weight (in particular the electronic management cards of the apparatus).

BRIEF DESCRIPTION OF THE DRAWINGS

FIG. 1 is a right ¾ perspective view of the apparatus within its protective casing.

FIG. 2 is a schematic left ¾ perspective view of the apparatus without the casing.

FIG. 3 is a schematic right ¾ perspective view of the apparatus without the casing, the upper half-frame being in the raised position.

FIG. 4 is a schematic right ¾ perspective view of the ion source access drawer in the open position.

FIG. 5 is a schematic left ¾ perspective view of the ion source access drawer in the closed position.

FIG. 6 is a schematic side view of the spectrometer chamber.

FIG. 7 is a front view of said chamber.

FIG. 8 is a view of the chamber in cross-section along line VII—VII.

DETAILED DESCRIPTION OF THE INVENTION

The apparatus in accordance with the invention is generally designated by the reference 1 in FIG. 1 and, in service, is covered and protected by a casing 2 of generally parallelepipedal shape which houses the entire unit. Said apparatus is connected on one side to the gas-phase chromatography device for introduction of the material to be analyzed and on the other side to dataprocessing control and display devices. In the casing 2, provision is made for lateral ventilation openings 3 and for the drawer or carriage 4 which gives access to the ion source.

Inside the casing 1, the apparatus comprises (FIGS. 2 and 3) a mechanically welded frame consisting of two stories : a first stationary sub-frame 5 constitutes the lower story on which is pivotally mounted a second sub-frame 6 which is movable and constitutes the upper story. The two sub-frames 5 and 6 are pivotally attached at the rear end by means of hinges 7 and the upper sub-frame 6 can be maintained in the oblique raised position by means of supporting jacks 8 (FIG. 3) so that the interior of the lower sub-frame can be perfectly accessible from the front end of the apparatus.

The upper sub-frame 6 houses substantially the entire electrical and electronic equipment including in particular a power supply unit 9, the high-frequency amplifier 10 and, at the front end, an electronic card tray 11 equipped with ventilating devices 12.

Within the lower sub-frame 5 are grouped together substantially the entire mechanical equipment including in particular the high-frequency transformer tank 13 on which is placed a spectrometer chamber 14 having a parallelepipedal external shape. The ion source is housed within a section located at the front end of the spectrometer chamber. Said front section is connected externally on one side to the interface 15 with the chromatographic apparatus and on the other side to a first turbomolecular pump 16. A second turboturbomolecular pump 17 is connected to the rear section of the spectrometer chamber 14 in which the quadrupole analyzer is located. The connections are made by means of coupling flanges. A mechanical forepump 18 is connected in series to the discharge end of the turbomolecular pumps 16 and 17 and is fixed on the sub-frame 5 at the rear end. Ventilating devices 19 are provided on each side of the sub-frame 5.

The spectrometer chamber 14 is provided with a heating device 20.

The front portion of the chamber 14 is closed by a movable cover 21 on which a plate 23 can be mounted with interposition of spacer members 22 and is intended to support a face plate 4 providing access to the source drawer. In the closed position, said plate 4 is located at the level of the casing 2 (as shown in FIG. 1).

The spectrometer chamber 14 (shown more clearly in FIGS. 6 to 8) is a machined block, for example of aluminum or of cast aluminum having a substantially parallelepipedal external shape and a substantially cylindrical internal shape. The internal portion has a front section 24 and a rear section 25 of slightly smaller diameter, these sections being separated by a small annular shoulder 26.

On a lateral face of the spectrometer chamber 14, orifices 27 and 28 surrounded by mounting holes 29 and 30 serve to mount turbomolecular pumps 16 and 17 by means of suitable coupling flanges.

On the other lateral face of the chamber 14, an orifice 31 receives the interface 15 with the chromatographic device.

An orifice 32 is formed in the bottom face of the chamber 14 and located in the rear portion 25 thereof which houses the analyzer. A block 33 is fitted in said orifice and adapted to carry two rigid connection pins 34 for the quadrupole filter.

The front opening 35 of the chamber 14 is circular and is surrounded by a groove in which is fitted a slightly projecting O-ring seal.

Bores parallel to the axis of the spectrometer chamber 14 are pierced in the chamber body at three of the corners which surround the opening 35. Two diagonally opposite bores 36 are intended to receive two guide rods 37 connected to the source drawer (FIG. 4). Within said bores 36 are provided ball-type slides or precision guides having a low coefficient of friction and permitting strictly accurate guiding of the rods. The third bore 38 receives the threaded driving rod 39 of the source drawer (FIG. 5).

The source drawer comprises on the one hand the plate 21 which ensures leak-tightness with the chamber 14 when said plate is applied on the seal which surrounds the opening 35 and, on the other hand, the rail 40 which is secured to the plate 21 and supports the ion source 41 as well as its optical system 42 and magnets 44 which generate the magnetic field for confinement of the source and, at the end of the rail, the differential pumping disk 43. When the drawer is closed, said disk 43 is intended to be applied by means of a ring rigidly fixed to the quadrupole filter against the annular shoulder 26 which separates the front and rear internal portions of the chamber 14 in order to maintain a different pressure (in a factor of 10) within the ion source compartment and within the analyzer compartment. Finally, the plate 21 also supports the guide rods 37 as well as the threaded driving rod 39. It will be noted that the ring of the quadrupole filter which is applied against the annular shoulder 26 is present within the apparatus which is employed in the chemical ionization mode but is dispensed with in the electron impact mode.

A driving motor 45 fixed beneath the spectrometer chamber 14 drives the threaded rod 39 by means of a reduction-gear unit 46 and serves to displace the source drawer in the forward or rearward direction when a suitable control is received.

In order to ensure that the cover-plate 21 is uniformly applied on the circumference of the seal, the threaded rod 39 is associated with a removable centering arm or latch 47 which is fixed by means of two notches 48 and 49, said notches being adapted to cooperate respectively with a precision-milled recess in the threaded rod 39 and with one of the spacer members 22. It is apparent that, when the arm is in position, it is coupled to the rod 39 for translational motion and is applied by means of a bearing screw 50 towards the center of the plate 21 during the drawer-closing operation. When the latch 47 is released by hand, this permits full withdrawal of the source drawer and therefore gives access to the quadrupole filter. This filter is held in position entirely within the spectrometer chamber 14, in the rear portion (and not in an overhung position by means of a flange attachment known in devices of the prior art), by means of a system of ball spacers which also permits displacement of the filter in sliding motion along the internal wall of the chamber up to its final position determined by grooves of the wall. The filter is connected to the pins 34. Apart from the fact that it is not subject to the parasitic vibrations of flexible connections, this short and rigid connection is useful in order to retain the high Q factor of the oscillating circuit constituted by the quadrupole filter forming the capacitance and the secondary winding of the transformer placed within the tank 13 which forms the inductance. It is therefore necessary to have a very low resistance in order to preserve this Q factor.

While the invention has been described with reference to a specific embodiment, the description is illustrative of the invention and is not to be construed as limiting the invention. Various modifications and applications may occur to those skilled in the art without departing from the true spirit and scope of the invention as defined by the appended claims.

What is claimed is:

1. A mass spectrometer with quadrupole filter comprising, within a frame closed by a casing, a spectrometer chamber which is intended to contain the ion source and its associated electron optical system, and a quadrupole filter, wherein the spectrometer chamber is designed in the form of a hollow sleeve closed at one end by a removable leak-tight cover mounted on a longitudinally-sliding motor-driven carriage which also supports the ion source and its optical system, the carriage being capable of selective displacement in translational motion between a closed position in which the ion source is in the work position and said cover is in the closed position, and an open position in which the carriage projects outside the casing at least to a partial extent and allows access to the ion source and its associated optical system.

2. A mass spectrometer according to claim 1, wherein the carriage is adapted to carry a second closure plate which is intended to provide a separation, when the carriage is in the closed position, between two compartments of the spectrometer chamber which are maintained at different pressures.

3. A mass spectrometer according to claim 1, wherein the carriage is mounted on at least one rod guided in translational motion by ball type slides.

4. A mass spectrometer according to claim 1, wherein the carriage is driven by a motor and a reduction-gear unit which are attached to the spectrometer chamber and drive a sliding threaded rod which is attached to the carriage.

5. A mass spectrometer according to claim 4, wherein the threaded rod is displaced off-center with respect to the cover but is associated with a bearing arm which is intended to center the closing force.

6. A mass spectrometer according to claim 1, wherein the spectrometer chamber has a body which is externally parallelepipedal and internally cylindrical, said body being provided in at least two of its corners with bores at least one of which is intended to receive a carriage-guiding rod, and wherein at least one of said bores is intended to receive a carriage-driving rod.

7. A spectrometer according to claim 6, wherein the body of the spectrometer chamber is made of machined material selected from the group consisting of solid metal and metal alloy.

8. A mass spectrometer according to claim 1, wherein the quadrupole filter is entirely housed within the spectrometer chamber and is maintained therein by means of spacer rings.

9. A mass spectrometer according to claim 8, wherein the quadrupole filter can be incorporated in or withdrawn from the spectrometer chamber through the end which is provided with the removable cover, and wherein the filter is connected to the high-frequency transformer by plugging onto short rigid pins.

10. A mass spectrometer according to claim 1, wherein the frame comprises two superposed sub-frames mounted in articulated relation and respectively housing essentially the mechanical elements and essentially the electrical and electronic elements.

11. A mass spectrometer according to claim 10, wherein the lower sub-frame houses a mechanical forepump connected to turbomolecular pumps which are connected to the spectrometer chamber.

12. A mass spectrometer according to claim 1, wherein the spectrometer chamber has a body which is externally parallelepipedal and internally cylindrical, said body being provided in at least two of its corners with bores which are intended to receive carriage-guiding rods.

13. A mass spectrometer according to claim 1, wherein the spectrometer chamber has a body which is externally parallelepipedal and internally cylindrical, said body being provided in at least two of its corners with bores which are intended to receive carriage-driving rods.

14. A mass spectrometer according to claim 6, wherein said body is provided in its diametrically opposed corners with correspondingly two bores for receiving two carriage-guiding rods, and wherein said body is provided in one of its remaining corners with a bore for receiving said carriage-driving rod.

15. A spectrometer according to claim 12, wherein the body of the spectrometer chamber is made of machined material selected from the group consisting of solid metal and metal alloy.

16. A spectrometer according to claim 13, wherein the body of the spectrometer chamber is made of machined material selected from the group consisting of solid metal and metal alloy.

17. A spectrometer according to claim 1, wherein the body of the spectrometer chamber is made of machined material selected from the group consisting of solid metal and metal alloy.

18. A mass spectrometer according to claim 1, wherein the carriage is mounted on at least one rod guided in translational motion by precision guides having low coefficient of friction.

* * * * *